US00PP36013P2

(12) United States Plant Patent
Bernuetz

(10) Patent No.: US PP36,013 P2
(45) Date of Patent: Jul. 16, 2024

(54) ***EUPHORBIA* PLANT NAMED 'BONPRI 1495'**

(50) Latin Name: ***Euphorbia pulcherrima* Willd. ex Klotzsch X *Euphorbia cornastra***
Varietal Denomination: Bonpri 1495

(71) Applicant: Andrew Bernuetz, Glenbrook (AU)

(72) Inventor: Andrew Bernuetz, Glenbrook (AU)

(73) Assignee: BONZA BOTANICALS PTY, LTD., Yellow Rock (AU)

( * ) Notice: Subject to any disclaimer, the term of this patent is extended or adjusted under 35 U.S.C. 154(b) by 0 days.

(21) Appl. No.: 18/384,222

(22) Filed: Oct. 26, 2023

(51) Int. Cl.
*A01H 5/12* (2018.01)
*A01H 6/38* (2018.01)

(52) U.S. Cl.
USPC ..... Plt./306

(58) Field of Classification Search
USPC ..... Plt./302, 303, 306
See application file for complete search history.

*Primary Examiner* — Susan McCormick Ewoldt
(74) *Attorney, Agent, or Firm* — C. Anne Whealy

(57) ABSTRACT

A new and distinct cultivar of *Euphorbia* plant named 'Bonpri 1495', characterized by its upright and mounded plant habit; vigorous growth habit; freely branching habit; large inflorescences with bright salmon pink-colored flower bracts; and good post-production longevity.

2 Drawing Sheets

Figure 1:
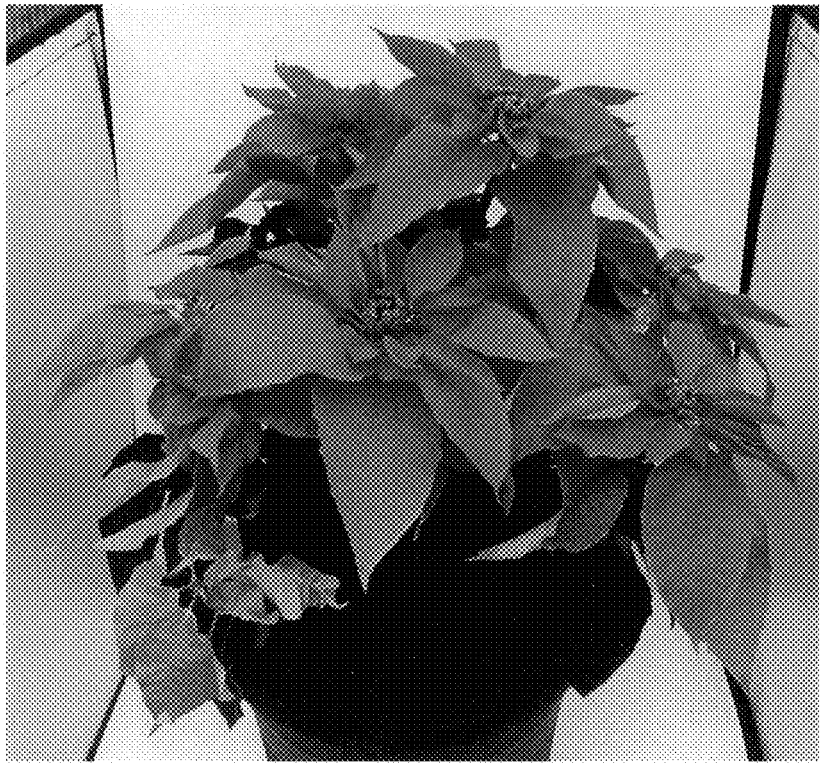

Botanical designation: *Euphorbia pulcherrima* Willd. ex Klotzsch X *Euphorbia cornastra.*

Cultivar denomination: 'BONPRI 1495'.

CROSS-REFERENCED TO CLOSELY-RELATED APPLICATIONS

Title: *Euphorbia* Plant Named 'Bonpri 1482'
Inventor/Applicant: Andrew Bernuetz
Filed: Oct. 26, 2023

BACKGROUND OF THE INVENTION

The present invention relates to a new and distinct cultivar of *Euphorbia* plant, an interspecific hybrid botanically known as *Euphorbia pulcherrima* Willd. ex Klotzsch X *Euphorbia cornastra*, and hereinafter referred to by the cultivar name 'Bonpri 1495'.

The new *Euphorbia* plant is a product of a planned breeding program conducted by the Inventor in Yellow Rock, New South Wales, Australia. The objective of the program is to create and develop new interspecific *Euphorbia* plants with compact, upright and mounded plant habit and attractive flower bracts.

The new *Euphorbia* plant is a naturally-occurring whole plant mutation of a proprietary selection of *Euphorbia pulcherrima* Willd. ex Klotzsch X *Euphorbia cornastra* identified as code number 1095, not patented. The new *Euphorbia* plant was discovered and selected by the Inventor as a single flowering plant from within a population of plants of the mutation parent selection in a controlled greenhouse environment in Yellow Rock, New South Wales, Australia in October, 2014.

Asexual reproduction of the new *Euphorbia* plant by terminal vegetative cuttings in a controlled greenhouse environment in Yellow Rock, New South Wales, Australia since October, 2014 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bonpri 1495'. These characteristics in combination distinguish 'Bonpri 1495' as a new and distinct *Euphorbia* plant:

1. Upright and mounded plant habit.
2. Vigorous growth habit.
3. Freely branching habit.
4. Large inflorescences with bright salmon pink-colored flower bracts.
5. Good post-production longevity.

Plants of the new *Euphorbia* differ primarily from plants of the mutation parent selection in flower bract color as flower bracts of plants of the new *Euphorbia* are lighter in color than flower bracts of plants of the mutation parent selection. In addition, plants of the new *Euphorbia* are more freely branching than plants of the mutation parent selection.

Plants of the new *Euphorbia* can be compared to plants of the *Euphorbia pulcherrima* Willd. ex Klotzsch X *Euphorbia cornastra* 'Bonpri 1482', disclosed in a U.S. Plant patent application Ser. No. 18/384,217, filed concurrently. In side-by-side comparisons, plants of the new *Euphorbia* differ primarily from plants of 'Bonpri 1482' in the following characteristics:

1. Plants of the new *Euphorbia* are somewhat shorter and broader than plants of 'Bonpri 1482'.
2. Plants of the new *Euphorbia* are more freely branching than plants of 'Bonpri 1482'.
3. Plants of the new *Euphorbia* fewer flower bracts per inflorescence than plants of 'Bonpri 1482'.

4. Plants of the new *Euphorbia* have smaller flower bracts per inflorescence than plants of 'Bonpri 1482'.
5. Plants of the new *Euphorbia* and 'Bonpri 1482' differ in flower bract color as flower bracts of plants of the new *Euphorbia* are bright salmon pink in color whereas flower bracts of plants of 'Bonpri 1482' are bright purplish red in color.

Plants of the new *Euphorbia* can also be compared to plants of the *Euphorbia pulcherrima* Willd. ex Klotzsch X *Euphorbia cornastra* 'Bonpri 1095', disclosed in U.S. Plant Pat. No. 28,676. In side-by-side comparisons, plants of the new *Euphorbia* differ primarily from plants of 'Bonpri 1095' in the following characteristics:

1. Plants of the new *Euphorbia* are broader than plants of 'Bonpri 1095'.
2. Plants of the new *Euphorbia* are more freely branching than plants of 'Bonpri 1095'.
3. Leaves of plants of the new *Euphorbia* are larger than leaves of plants of 'Bonpri 1095'.
4. Leaves of plants of the new *Euphorbia* are lanceolate in shape whereas leaves of plants of 'Bonpri 1095' are deltoid or ovate in shape.
5. Plants of the new *Euphorbia* have more flower bracts per inflorescence than plants of 'Bonpri 1095'.
6. Plants of the new *Euphorbia* have smaller flower bracts per inflorescence than plants of 'Bonpri 1095'.
7. Flower bracts of plants of the new *Euphorbia* are lanceolate in shape whereas flower bracts of plants of 'Bonpri 1095' are ovate in shape.
8. Plants of the new *Euphorbia* and 'Bonpri 1095' differ in flower bract color as flower bracts of plants of the new *Euphorbia* are bright salmon pink in color whereas flower bracts of plants of 'Bonpri 1095' are red purple in color with lighter red purple-colored margins.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph on the first sheet (FIG. 1) is a side perspective view of a typical flowering plant of 'Bonpri 1495' grown in a container.

Figure 2:
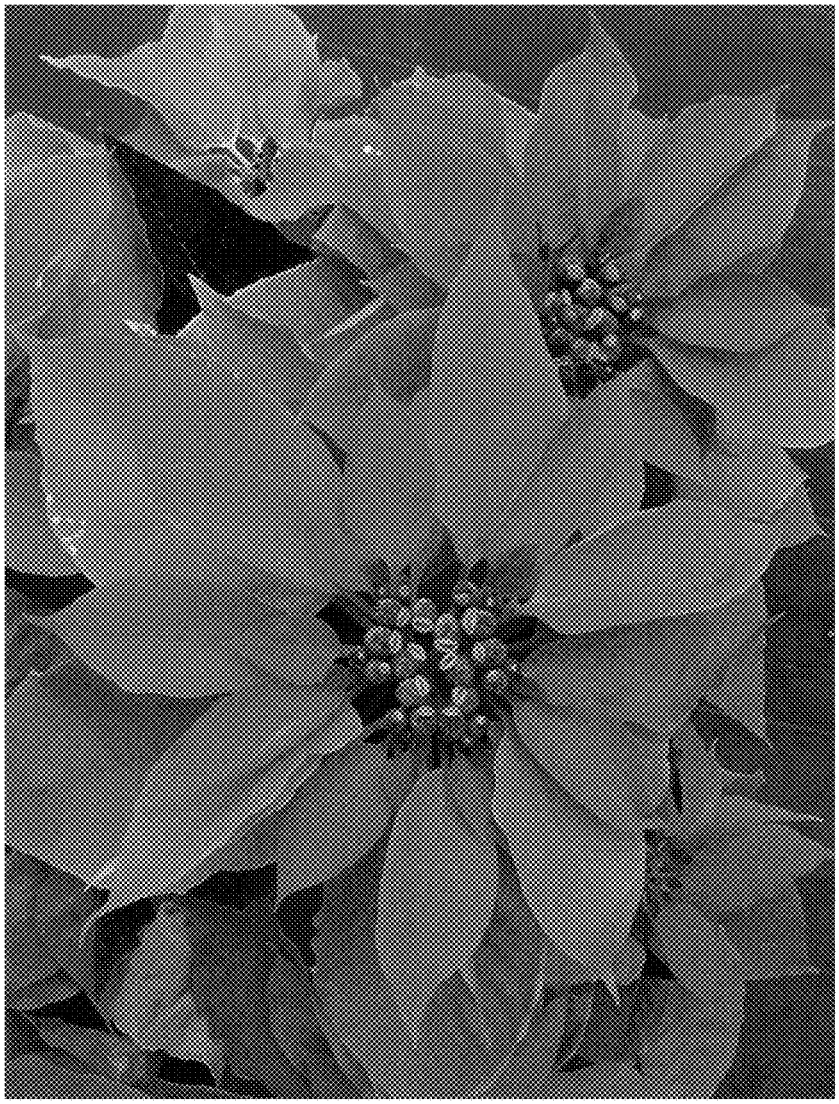

The photograph on the second sheet (FIG. 2) is a close-up view of a typical flowering plant of 'Bonpri 1495'.

DETAILED BOTANICAL DESCRIPTION

Plants used in the aforementioned photographs and described herewith in detail were grown during the autumn and early winter in 10.5-cm containers in an outdoor nursery in Higashiomi, Shiga, Japan and under cultural practices typical of commercial *Euphorbia* production. During the production of the plants, day temperatures averaged 23 C and night temperatures averaged 13 C. Plants were six months old when the photographs and the description were taken. In the following description, color references are made to The Royal Horticultural Society Colour Chart, 2015 Edition, except where general terms of ordinary dictionary significance are used.

Botanical classification: *Euphorbia pulcherrima* Willd. ex Klotzsch X *Euphorbia cornastra* 'Bonpri 1495'.

Parentage: Naturally-occurring whole plant mutation of a proprietary selection of *Euphorbia pulcherrima* Willd. ex Klotzsch X *Euphorbia cornastra* identified as code number 1095, not patented.

Propagation:

*Type*.—Terminal vegetative cuttings.

*Time to initiate roots, summer*.—About ten days at temperatures about 20 C to 21 C.

*Time to initiate roots, winter*.—About twelve days at temperatures about 20 C to 21 C.

*Time to produce a rooted young plant, summer*.—About 24 days at temperatures about 20 C to 21 C.

*Time to produce a rooted young plant, winter*.—About 28 days at temperatures about 20 C to 21C.

*Root description*.—Fibrous; typically white in color, actual color of the roots is dependent on substrate composition, water quality, fertilizers, substrate temperature and physiological age of roots.

*Rooting habit*.—Freely branching; medium density.

Plant description:

*Plant habit and form*.—Upright and mounded plant habit; inverted triangle; inflorescences positioned above the foliar plane; vigorous growth habit.

*Plant height*.—About 31.3 cm.

*Plant diameter or spread*.—About 49.3 cm.

*Lateral branch description*.—Branching habit: Freely branching habit, about eight lateral branches develop per plant. Length: About 17.8 cm. Diameter: About 5.6 mm. Internode length: About 4.25 cm. Aspect: Mostly upright to somewhat outward. Strength: Moderately strong. Texture and luster: Smooth, glabrous; glossy. Color: Close to 144A.

*Leaf description*.—Arrangement: Alternate, simple. Length: About 9.1 cm. Width: About 5.6 cm. Shape: Lanceolate. Apex: Acute. Base: Rounded. Margin: Mostly entire, occasionally with few shallow lobes. Venation pattern: Pinnate, reticulate. Texture and luster, upper and lower surfaces: Smooth, glabrous; matte. Color: Developing leaves, upper surface: Close to 139A. Developing leaves, lower surface: Close to 139B. Fully developed leaves, upper surface: Close to 139A; venation, close to 144A. Fully developed leaves, lower surface: Close to 139B; venation, close to 144B. Petioles: Length: About 2.7 cm. Diameter: About 2.1 mm. Texture, upper and lower surfaces: Smooth, glabrous. Color, upper and lower surfaces: Close to 144A.

Inflorescence description:

*Inflorescence type and habit*.—Inflorescences are compound corymbs of cyathia with numerous flower bracts subtending the cyathia; inflorescences positioned above the foliar plane.

*Quantity of inflorescences*.—One per lateral branch, about eleven inflorescences develop per plant.

*Inflorescence diameter*.—About 21 cm.

*Inflorescence height*.—About 7.1 cm.

*Fragrance*.—None detected.

*Natural flowering season*.—Plants typically flower during the autumn and winter in Japan; inflorescence initiation and development can also be induced under artificial long nyctoperiod and short photoperiod conditions; early flowering response, plants flower about 50 to 56 days under natural season or photoinductive conditions in Japan.

*Post-production longevity*.—Good post-production longevity; plants of the new *Euphorbia* maintain good substance and bract color for about six to eight weeks.

*Flower bracts*.—Quantity per inflorescence: About 14. Length, largest bracts: About 5.1 cm. Width, largest bracts: About 2.6 cm. Aspect: Mostly horizontal and flat. Shape: Lanceolate. Apex: Acute. Base: Obtuse. Margin: Entire. Texture and luster, upper and lower surfaces: Smooth, glabrous; matte. Venation pattern: Pinnate, reticulate. Color: Transitional bracts, upper surface: Random sectors, close to 138A and N57D. Transitional bracts, lower surface: Random sectors, close to 138B and 56A. Developing and fully expanded bracts, upper surface: Close to 58B; venation, close to N57C; flower bracts resist fading with subsequent development. Fully expanded bracts, lower surface: Close to 58C; venation, close to 58A; flower bracts resist fading with subsequent development. Flower bract petioles: Length: About 1 cm. Diameter: About 1.4 mm. Texture, upper and lower surfaces: Smooth, glabrous. Color, upper and lower surfaces: Close to 138B tinged with N57B.

*Cyathia*.—Quantity per corymb: About 23. Diameter of cyathia cluster: About 2.8 cm. Height, individual cyathium: About 6.5 mm. Diameter, individual cyathium: About 5.5 mm. Shape, individual cyathium: Globose. Color: Distally, close to 63A and proximally, close to N144A. Nectaries: Quantity per cyathium: About 13. Size: About 2.3 mm by 5 mm. Texture: Smooth, glabrous. Color: Close to 13A.

*Peduncles*.—Length: About 2.2 mm. Diameter: About 2.1 mm. Texture, upper and lower surfaces: Smooth, glabrous. Aspect: Mostly upright. Color, upper and lower surfaces: Close to 145A.

*Reproductive organs*.—To date, stamen and pistil development have not been observed on plants of the new *Euphorbia*.

*Seeds and fruits*.—To date, seed and fruit development have not been observed on plants of the new *Euphorbia*.

Pathogen & pest resistance: To date, plants of the new *Euphorbia* have not been shown to be resistant to pathogens and pests common to *Euphorbia* plants.

Temperature tolerance: Plants of the new *Euphorbia* have been observed to tolerate temperatures ranging from about 8 C to about 40 C.

It is claimed:

1. A new and distinct *Euphorbia* plant named 'Bonpri 1495' as illustrated and described.

* * * * *